US006436415B2

(12) United States Patent
Levin

(10) Patent No.: US 6,436,415 B2
(45) Date of Patent: Aug. 20, 2002

(54) HERBAL DEODORANT

(75) Inventor: Ezra Levin, Ra'anana (IL)

(73) Assignee: Hlavin Industries, Ltd. (IL)

( * ) Notice: Subject to any disclaimer, the term of this patent is extended or adjusted under 35 U.S.C. 154(b) by 0 days.

(21) Appl. No.: 09/775,107

(22) Filed: Feb. 1, 2001

Related U.S. Application Data

(63) Continuation of application No. PCT/IL99/00415, filed on Jul. 28, 1999.

(30) Foreign Application Priority Data

Aug. 4, 1998 (IL) ................................................. 125655

(51) Int. Cl.$^7$ ............................ A61K 6/00; A61K 7/32; A61K 7/38; A01N 65/00; A01N 25/00
(52) U.S. Cl. .................. 424/401; 424/725; 424/65; 424/68; 514/944; 514/945; 514/951
(58) Field of Search ................................. 424/401, 725, 424/65, 68; 514/944, 945, 951

(56) References Cited

U.S. PATENT DOCUMENTS

| | | | |
|---|---|---|---|
| 4,002,775 A | 1/1977 | Kabara | 426/532 |
| 4,921,694 A | 5/1990 | Hoppe et al. | 424/65 |
| 5,098,694 A | 3/1992 | Komp et al. | 424/47 |
| 5,260,053 A | 11/1993 | Chappell et al. | 424/65 |

FOREIGN PATENT DOCUMENTS

| | | |
|---|---|---|
| DE | 23 51 864 | 4/1975 |
| DE | 23 51 927 | 4/1975 |
| DE | 23 54 517 | 5/1975 |
| EP | 0 376 761 | 7/1990 |
| FR | 2 504 551 | 10/1982 |
| GB | 1475226 | 6/1977 |
| GB | 2 262 887 A | 7/1993 |
| JP | 63-264516 | 11/1988 |
| JP | 01068264 A * | 3/1989 |
| JP | 05269186 A * | 10/1993 |
| JP | 06190027 A * | 7/1994 |
| JP | 07171209 A * | 7/1995 |
| RU | 971333 | 11/1982 |
| WO | WO97/18823 | 5/1997 |

OTHER PUBLICATIONS

JPO (U–1) and Derwent (U–2) abstracts, Shoji et al., JP–05269186–A, Oct. 1993.*
JPO (V–1) and Derwent (V–2) abstracts, Ota, JP–06190027–A, Jul. 1994.*
JPO abstract, Mizobuchi, JP–07171209–A, Jul. 1995.*
JPO abstract, Yamamoto et al., JP–01068264–A, Mar. 1989.*

* cited by examiner

*Primary Examiner*—Michael G. Hartley
*Assistant Examiner*—Michael A Willis
(74) *Attorney, Agent, or Firm*—Harness, Dickey & Pierce. P.L.C.

(57) ABSTRACT

A deodorant composition with active antibacterial constituents comprising on a weight basis the plant extracts of Myrtus from about 2% to about 8%, *Laurus nobilis,* from about 1% to 5% Drosera extract from about 1% to 7%, Myrrhis resin from about 3% to about 6%, and water 74% to 93%. Preferably, the composition is free of alcohol and aluminum.

30 Claims, No Drawings

HERBAL DEODORANT

This application is a continuation of previously filed PCT application Ser. No. PCT/IL99/00415, filed Jul. 28, 1999 which prior application was published in the English language of Feb. 17, 2000.

BACKGROUND OF THE INVENTION

The invention relates to a deodorant composition, employing only natural bacterides for personal use.

To be effective, a personal deodorant must reduce odor. It is known that odor from perspiration is caused by bacteria metabolizing the rich supply of proteins and lipids supplied by the apocrine sweat glands. Gram positive lipophilic diphtheroids and micrococci have been identified as the bacterial flora causing the odor in the armpit. The diphtheroids produce the typical pungent axillary odor and the micrococci produce a sweaty isovaleric acid type odor. Moisture and minerals secreted by the eccrine sweat glands serve to enrich and replenish axilla flora.

In order for a deodorant to work properly, it must:

a) Adhere to the skin and resist washing away easily with sweat, b) Sufficiently reduce populations of diphtheroids and micrococci and their subsequent metabolic end products, and c) Mask the presence of androgen steroids (produced by bacteria) which are detectable by the human nose at very low concentrations.

The use of natural bactericides is known in the art. For example, Kabara U.S. Pat. No. 4,002,775 and Hoppe et al. U.S. Pat. No. 4,921,694 describe lauroyl monoesters of glycerin and synergistic mixtures having antibacterial activity. Also EP Patent Publication No. 376761, German Patent Nos. 23 54 517, 23 51 927 and 2351 864, United Kingdom Patent Publication No. 1,475,226 describe the deodorizing effects of lichen acid, and especially usnic acid. A herbal deodorant was disclosed in U.S. Pat. No. 5,260,053. A natural deodorant composition was patented in U.S. Pat. No. 5,098,694. JP 63 264516 A (Lion Corp) (Derwent WPI 89-091239) discloses deodorizing effects of plant extracts from e.g. Myrtaceae and Lauraceae among others.

SUMMARY OF THE INVENTION

It is an object of the invention to provide a deodorant composition that has active antibacterial constituents consisting essentially of natural plant extracts, and that is essentially free of alcohols and aluminum.

According to one aspect of the invention, the deodorant composition comprises a liquid roll-on deodorant. According to another aspect of the invention, the deodorant can be in the form of a stick deodorant. It is also possible to formulate deodorant compositions in accordance with the invention in the form of a spray, cream, ointment or powder.

The main active ingredients in the deodorant composition according to the invention are the plant extracts of a) Myrtus (myrtle), b) laurus nobilis (sweet bay), Drosera (sundew) and Myrrhis resin. Pinus sibirica resin may be substitutes for myrrhis resin. By Drosera we include Drosera rotundifolia and Drosera longustifolia. The remainder of the composition constitutes the carrier which is basically inactive as a deodorant.

The carrier is preferably only water but may also contain fragrances. Deodorants which contain fragrances, for example, may be more commercially popular. Various known natural cosmetically acceptable ingredients may be added to counteract skin irritation.

Suitable salts are potassium hydroxide, sodium hydroxide, and potassium-, sodium-, ammonium carbonate, or ammonium hydroxide.

Preservatives such as parabens, and stabilizers such as antioxidants and UV-filter substances e.g. benzophenones or thickeners such as hydroxypropylcellulose may be added.

As was mentioned earlier, the deodorant composition of the invention contains plant extracts of Myrtus and *Laurus nobilis* with Drosera extract as synergist and Myrrhis resin which absorbs the color of the other active ingredients.

The carrier may contain the following ingredients and ranges:

humectant/solvent up to 40%
salt up to 0.5%
fragrance up to 5%
emollient up to 10%
water up to 95%

The composition of the invention is made by simply mixing together the appropriate ingredients in the usual manner and placing the composition in the desired vehicle for administration.

DETAILED DESCRIPTION OF THE INVENTION

The deodorant composition of this invention has active antibacterial constituents consisting essentially of natural materials. In a preferred embodiment of this aspect of the invention, the deodorant composition for liquid roll-on and stick deodorants consists essentially of the following ingredients, with the preferred ranges given by weight percent: (a) Myrtus [Mytrus] extract, about 2% to 8%, preferably about 3% to 6%, and more preferably about 4%; and (b) extract of *Laurus nobilis* about 1% to 5%, preferably about 2% to 4%, and more preferably about 3%. In addition, the deodorant composition contains (c) extract of *Drosera* about 1% to 7%, preferably about 2% to 5%, and most preferably about 4% and/or resin of *Myrrhis* 3% to 6%, preferably about 4% to 5%, and most preferably about 4.5%. The composition also preferably contains 0.2% to 0.8% SEPIGEL, a mixture of polyacrylamide, $C_{13-14}$ isoparaffin and laureth-7 sold by Seppic Corporation.

The invention will be described in connection with the following examples.

EXAMPLE 1

A deodorant composition was made as set forth below:

| INGREDIENTS | WT |
| --- | --- |
| Extract of Myrtus | 4.5% |
| Extract of *Laurus nobilis* | 3.0% |
| Extract of Drosera | 3.0% |
| Resin of Myrrhis | 4.0% |
| Fragrance | 1% |
| SEPIGEL | 0.5% |
| Water | to 100% |

EXAMPLE 2

The following formulation was made up for a deodorant spray:

| INGREDIENTS | WT |
| --- | --- |
| Extract of Myrtus | 3.5% |
| Extract of *Laurus nobilis* | 2.5% |
| Resin of Myrrhis | 3.5% |
| Fragrance | 1.0% |
| SEPIGEL | 0.5% |
| Water | to 100% |

EXAMPLE 3

The following composition was made up for a roll-on formulation.

| INGREDIENTS | WT |
| --- | --- |
| Extract of Myrtus | 3.5% |
| Extract of *Laurus nobilis* | 2.5% |
| Extract of Drosera | 3.5% |
| Fragrance | 1% |
| Water | to 100% |

It will be appreciated by persons skilled in the art that the scope of the present invention is not limited to what has been shown and described hereinabove, merely by way of example. Rather, the scope of the invention is limited solely by the claims which follow.

What is claimed is:

1. A deodorant composition with active antibacterial constituents comprising the plant extracts of Myrtus 2% to about 8%, *Laurus nobilis* 1% to 5%, Drosera extract at a level of from about 1 to 7%, Myrrhis resin at a level of from about 3 to about 6%, and water.

2. A deodorant composition as in claim 1, comprising, on a weight basis, the plant extracts of Myrtus at a level of from about 3% to 6%, *Laurus nobilis at a level of from about* 2% to about 4%, Drosera at a level of from about 2 to about 5%, Myrrhis resin at a level of from about 4 to about 5%.

3. A deodorant composition of claim 2, comprising, on a weight basis, the plant extracts of Myrtus at a level of about 4%, *Laurus nobilis* at a level of about 3%, Drosera at a level of about 4%, and Myrrhis resin at a level of about 4.5%.

4. A deodorant composition with active antibacterial constituents comprising, on a weight basis, the plant extracts of Myrtus at a level of from about 2% to about 8%, *Laurus nobilis* 1% to 5%, Drosera at a level of from about 1 to 7%, Myrrhis resin at a level of from about 3 to about 6%, and water, wherein said composition is essentially free of alcohols and aluminum.

5. A composition of claim 1, additionally comprising from about 0.2% to about 0.8% by weight thickening agent.

6. A composition of claim 2, additionally comprising from about 0.2% to about 0.8% by weight thickening agent.

7. A composition of claim 3, additionally comprising from about 0.2% to about 0.8% by weight thickening agent.

8. A composition of claim 4, additionally comprising from about 0.2% to about 0.8% by weight thickening agent.

9. A composition of claim 1, additionally comprising from about 0.2% to about 0.8% by weight a mixture of polyacrylamide $C_{13-14}$ isoparaffin and laureth-7.

10. A composition of claim 2, additionally comprising from about 0.2% to about 0.8% by weight a mixture of polyacrylamide $C_{13-14}$ isoparaffin and laureth-7.

11. A composition of claim 3, additionally comprising from about 0.2% to about 0.8% by weight a mixture of polyacrylamide $C_{13-14}$ isoparaffin and laureth-7.

12. A composition of claim 4, additionally comprising from about 0.2% to about 0.8% by weight a mixture of polyacrylamide $C_{13-14}$ isoparaffin and laureth-7.

13. A composition of claim 1, which is a roll-on deodorant.

14. A composition of claim 1, which is a stick deodorant.

15. A composition of claim 1, which is a spray deodorant.

16. A composition of claim 2, which is a roll-on deodorant.

17. A composition of claim 2, which is a stick deodorant.

18. A composition of claim 2, which is a spray deodorant.

19. A composition of claim 3, which is a roll-on deodorant.

20. A composition of claim 3, which is a stick deodorant.

21. A composition of claim 3, which is a spray deodorant.

22. A composition of claim 4, which is a roll-on deodorant.

23. A composition of claim 4, which is a stick deodorant.

24. A composition of claim 4, which is a spray deodorant.

25. A composition of claim 5, which is a roll-on deodorant.

26. A composition of claim 5, which is a stick deodorant.

27. A composition of claim 5, which is a spray deodorant.

28. A composition of claim 9, which is a roll-on deodorant.

29. A composition of claim 9, which is a stick deodorant.

30. A composition of claim 9, which is a spray deodorant.

* * * * *